US008623036B2

(12) United States Patent
Harrison et al.

(10) Patent No.: US 8,623,036 B2
(45) Date of Patent: *Jan. 7, 2014

(54) MAGNAMOSIS

(71) Applicant: The Regents of the University of California, Oakland, CA (US)

(72) Inventors: Michael R. Harrison, San Francisco, CA (US); Dillon A. Kwiat, San Francisco, CA (US); Richard J. Fechter, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/832,919

(22) Filed: Mar. 15, 2013

(65) Prior Publication Data
US 2013/0253548 A1    Sep. 26, 2013

Related U.S. Application Data (63) Continuation-in-part of application No. 13/428,122, filed on Mar. 23, 2012, now abandoned, which is a continuation of application No. 12/189,330, filed on Aug. 11, 2008, now Pat. No. 8,142,454, which is a continuation-in-part of application No. 11/677,700, filed on Feb. 22, 2007, now Pat. No. 8,439,915, which is a continuation-in-part of application No. 11/431,416, filed on May 9, 2006, now abandoned, which is a continuation-in-part of application No. 10/954,995, filed on Sep. 29, 2004, now Pat. No. 8,043,290.

(60) Provisional application No. 61/614,630, filed on Mar. 23, 2012.

(51) Int. Cl.
*A61B 17/08* (2006.01)

(52) U.S. Cl.
USPC .......................................................... 606/153

(58) Field of Classification Search
USPC ......... 606/112, 118, 151, 153, 155, 156, 167, 606/171, 179, 180, 185, 186, 188, 189; 335/285, 302–306; 600/36, 12; 604/22; 403/DIG. 1; 30/74, 113.1–113.3, 30/114–115; 24/303
See application file for complete search history.

(56) References Cited

U.S. PATENT DOCUMENTS

| | | | | |
|---|---|---|---|---|
| 3,324,521 A * | 6/1967 | Humiston | ....................... | 24/303 |
| 3,372,443 A * | 3/1968 | Daddona, Jr. | ................... | 24/303 |
| 4,598,712 A * | 7/1986 | Rebuffat et al. | .............. | 606/153 |
| 4,931,057 A * | 6/1990 | Cummings et al. | ........... | 606/153 |
| 4,966,602 A * | 10/1990 | Rebuffat et al. | .............. | 606/154 |
| 5,330,486 A * | 7/1994 | Wilk | ............................. | 606/139 |
| 5,595,562 A * | 1/1997 | Grier | ............................. | 600/12 |
| 5,690,656 A * | 11/1997 | Cope et al. | ..................... | 606/153 |
| 7,374,567 B2 * | 5/2008 | Heuser | .......................... | 606/185 |

(Continued)

*Primary Examiner* — Ryan Severson
*Assistant Examiner* — David Eastwood
(74) *Attorney, Agent, or Firm* — Lumen Patent Firm (57) ABSTRACT

A magnamosis system for auto-anastomosing a region of the body using implants with magnetic members that may be individually delivered to different locations in the body. The implants with their magnetic members have a mating surface and polar alignment that generates an attractive force to compress tissue in the region between them. The tissue in the region necroses as a result of the compressive force such that tissue surrounding the necrosed tissue heals together to form an anastomosis.

16 Claims, 11 Drawing Sheets

(56) References Cited

U.S. PATENT DOCUMENTS

| | | | |
|---|---|---|---|
| 8,142,454 B2* | 3/2012 | Harrison et al. | 606/153 |
| 2002/0072758 A1* | 6/2002 | Reo et al. | 606/153 |
| 2002/0103495 A1* | 8/2002 | Cole | 606/153 |
| 2007/0118158 A1* | 5/2007 | Deem et al. | 606/153 |
| 2007/0173878 A1* | 7/2007 | Heuser | 606/185 |
| 2008/0108860 A1* | 5/2008 | Bell et al. | 600/12 |
| 2008/0114384 A1* | 5/2008 | Chang et al. | 606/153 |
| 2010/0036399 A1* | 2/2010 | Viola | 606/153 |

* cited by examiner

MAGNAMOSIS

CROSS-REFERENCE TO RELATED APPLICATIONS

This application claims priority from U.S. Provisional Patent Application 61/614,630 filed Mar. 23, 2012, which is incorporated herein by reference.

This application is a continuation-in-part of U.S. patent application Ser. No. 13/428,122 filed Mar. 23, 2012. U.S. patent application Ser. No. 13/428,122 filed Mar. 23, 2012 is a continuation of U.S. patent application Ser. No. 12/189,330 filed Aug. 11, 2008, which is incorporated herein by reference. U.S. patent application Ser. No. 12/189,330 filed Aug. 11, 2008 is a continuation-in-part of U.S. patent application Ser. No. 11/677,700 filed Feb. 22, 2007, incorporated herein by reference in its entirety, which is a continuation-in-part of U.S. patent application Ser. No. 11/431,416 filed on May. 9, 2006, incorporated herein by reference in its entirety, which is a continuation-in-part of U.S. patent application Ser. No. 10/954,995 filed on Sep. 29, 2004, incorporated herein by reference in its entirety.

FIELD OF THE INVENTION

The invention relates to methods, devices and systems for performing anastomosis. In particular, the invention relates to magnamosis devices, which are devices for performing anastomosis using magnets for applying compressive force between two structures.

BACKGROUND OF THE INVENTION

Anastomosis is the connection of two structures. It refers to connections between blood vessels or between other tubular structures such as loops of intestine. An example of surgical anastomosis occurs when a segment of intestine is resected and the two remaining ends are sewn or stapled together (anastomosed) to re-establish continuity of the bowel, for example Roux-en-Y anastomosis. The procedure is referred to as intestinal anastomosis. The present invention advances the art by providing new devices to perform anastomosis.

SUMMARY OF THE INVENTION

A magnamosis system is provided for performing an anastomosis. The system has two implants each distinguishing a casing with a magnet. The magnets are of opposite polarity. The casings have mating surfaces. A first implant defines a convex mating surface, and the convex mating surface has a first radius. The second implant defines a concave mating surface and the concave mating surface extends within the body of the second implant. The concave mating surface has a second radius, such that the second radius is greater than the first radius.

While the convex mating surface faces the concave mating surface, a magnetic mating of the surfaces, caused by the magnets, causes the convex mating surface of the first implant to extend within the body of the second implant and apply a non--uniform compressive force across two adjacent structures disposed in between the two mating surfaces. The non-uniform compressive force is capable of forming an anastomosis between the two adjacent structures.

To ensure the magnamosis system is exerting a force above a certain threshold, an additional element that measures force, distance or some other relatable measurement could be included in magnamosis implants. Accordingly, various examples are provided with force sensors. Furthermore, embodiment of the implants could have different forms, shapes and sizes as well as implants with or without through holes.

DETAILED DESCRIPTION

Figure 1:
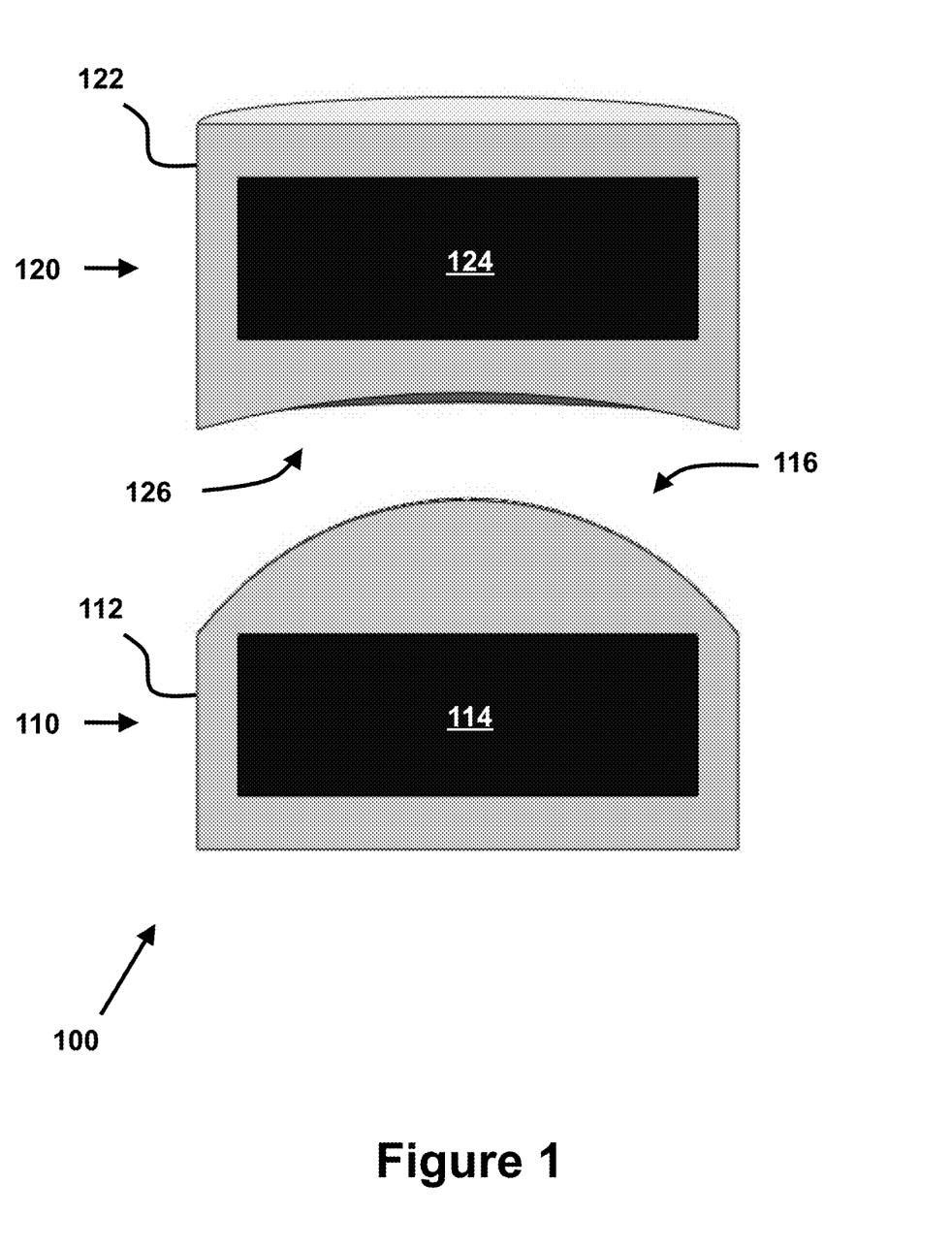
FIG. 1 shows a magnamosis system 100 with a first implant 110 and a second implant 120 for performing an anastomosis according to an exemplary embodiment of the invention. Both implants 110 and 120 are without through holes.

FIG. 1 shows a magnamosis system 100 with a first implant 110 and a second implant 120. First implant 110 has a first casing 112 (defining a body) that encloses a first magnet 114 with a first magnetic polarity. First casing 112 defines a convex mating surface 116 with a first radius.

Second implant 120 has a second casing 122 (defining a body) that encloses a second magnet 124 with a second magnetic polarity opposite from the first magnetic polarity. Second casing 122 defines a concave mating surface 126 that extends within the body of the second implant 120. Concave mating surface 126 has a second radius, whereby the second radius is greater than the first radius as shown in FIG. 1. In one example, the convex mating surface is a single convex mating surface and the concave mating surface is a single concave mating surface.

While the convex mating surface 116 faces the concave mating surface 126, a magnetic mating of the two surfaces, caused by the two magnets, causes the convex mating surface 116 of the first implant 110 to extend within the body of the second implant 120 and apply a non-uniform compressive force across two adjacent structures disposed in between the two mating surfaces. The non-uniform compressive force is capable of forming an anastomosis between the two adjacent structures. In addition, the non-uniform compressive force across the two adjacent structures increases radially inward toward the center of the two surfaces.

One of the possibly complicating clinical issues with the use of the magnamosis system for creating compression anastomosis in e.g. a bowel is for the surgeon to know that the system is exerting enough force to ensure a proper anastomosis formation. In certain circumstances, if the bowel is too thick, an anastomosis could not form correctly. To ensure the magnamosis system is exerting a force above the known threshold, an additional element that measures force, distance or some other relatable measurement could be included in magnamosis implants.

Figure 2:
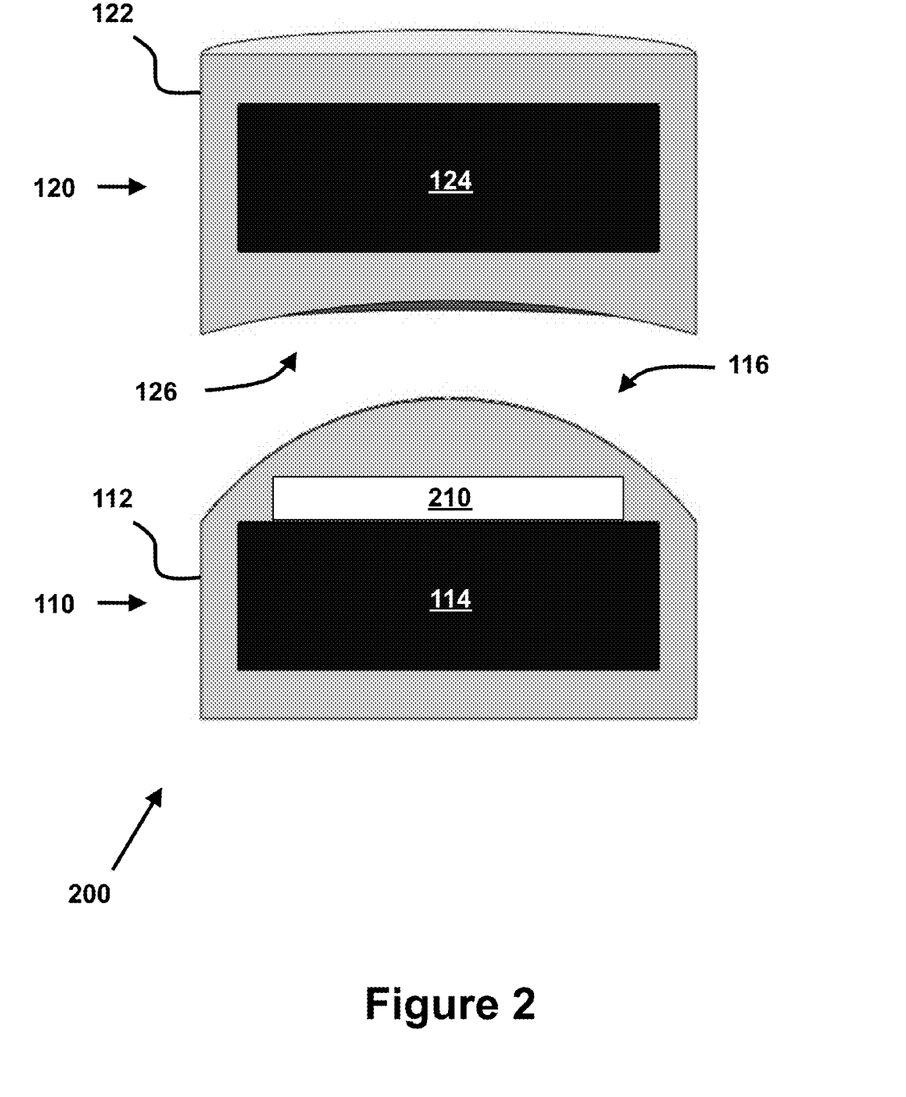
FIGS. 2-4 show magnamosis systems 200, 300 and 400 similar to magnamosis system 100 with the difference of also having force sensors 210, 310 and 410, respectively.
Figure 3:
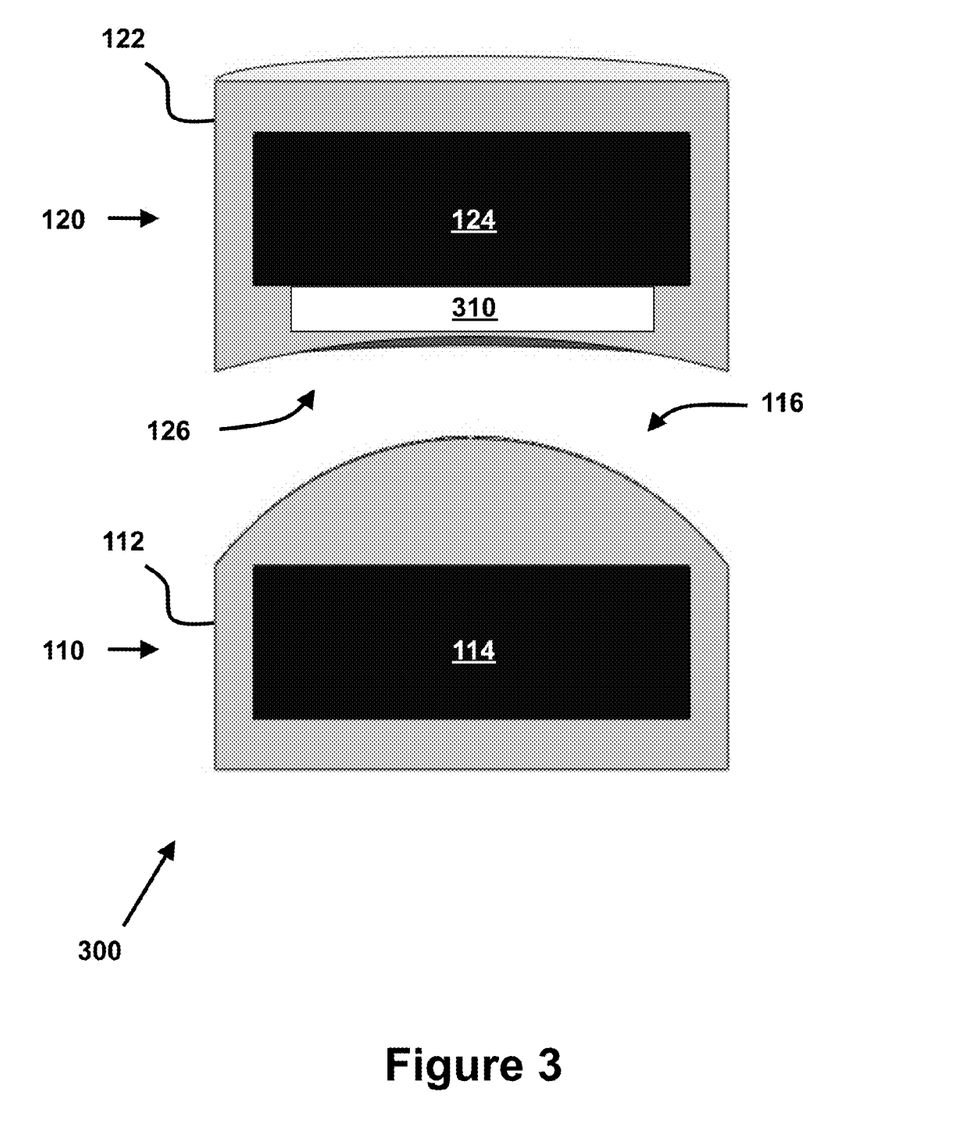
Figure 4:
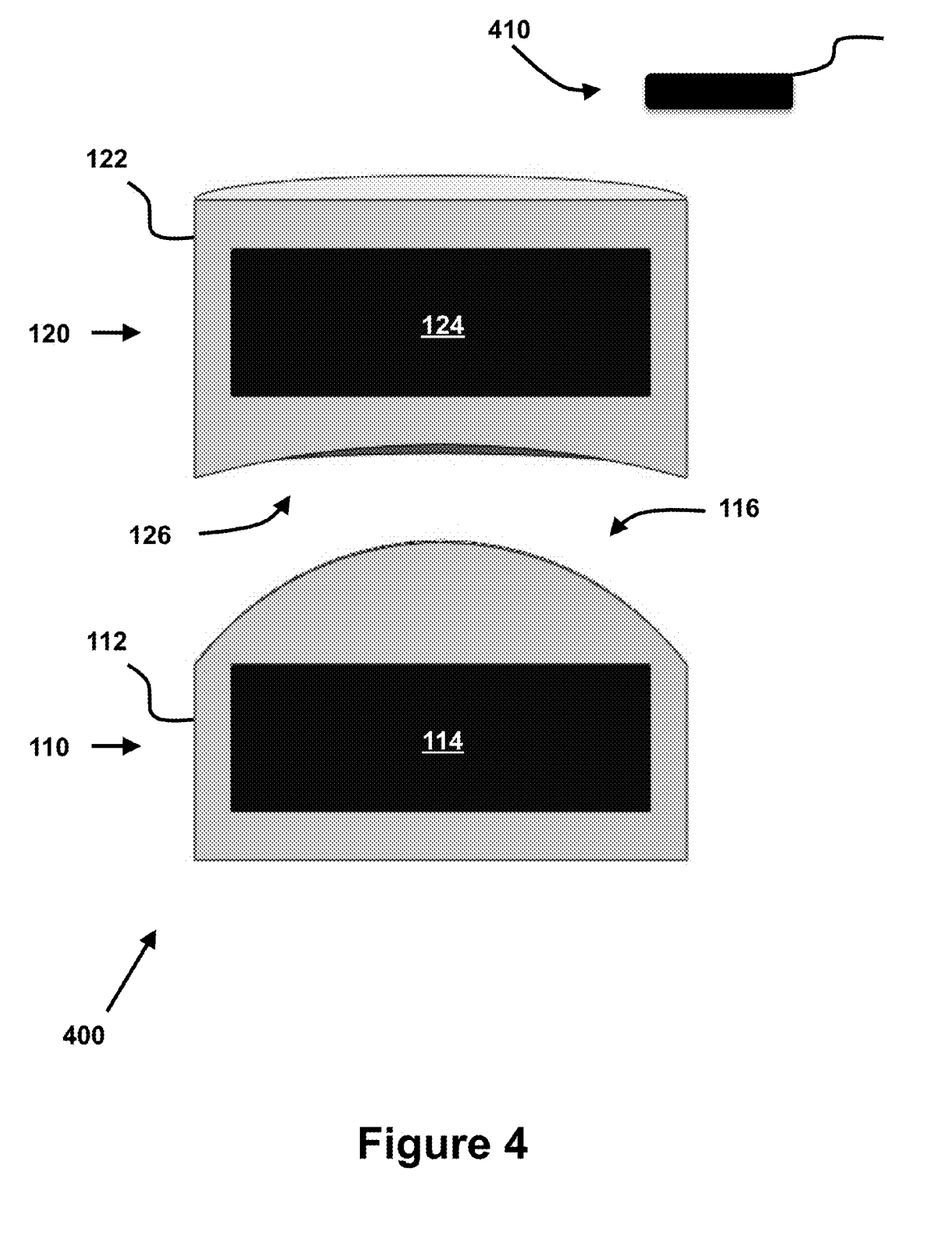
Figure 5:
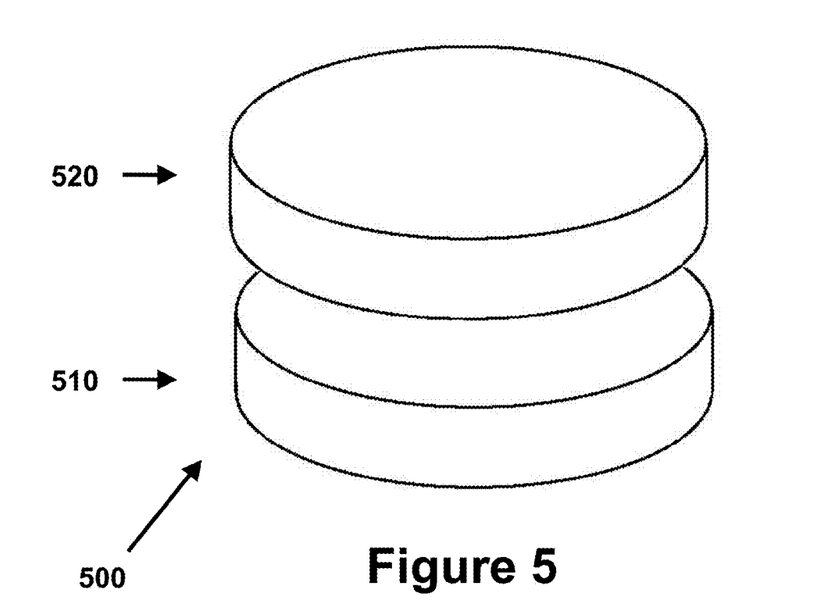
FIG. 5 shows according to an exemplary embodiment of the invention a view of magnamosis system 500. Both implants 510 and 520 are without through holes.
Figure 6:
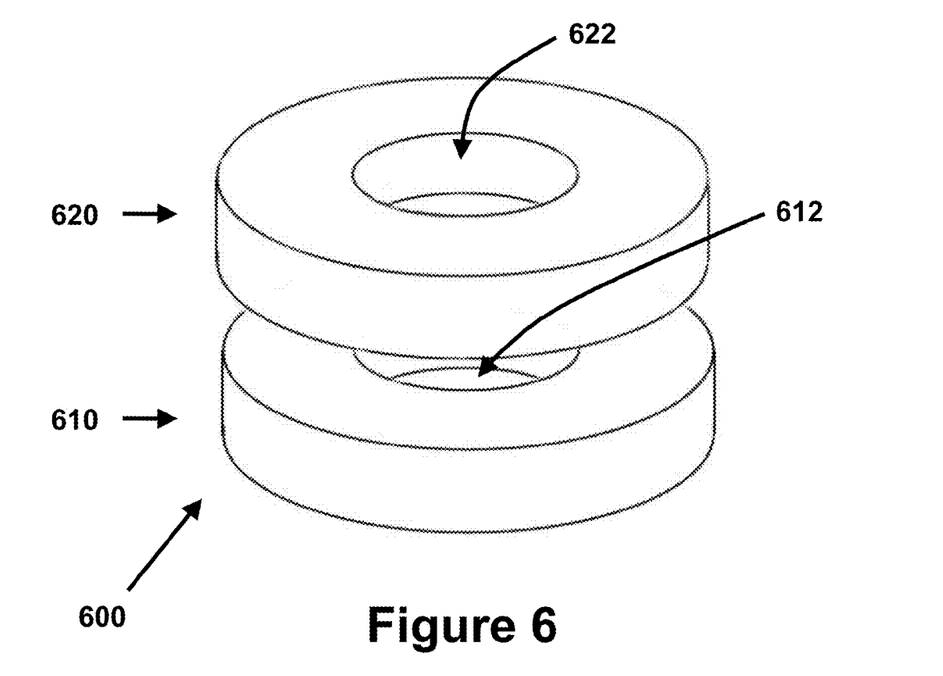
FIG. 6 shows according to an exemplary embodiment of the invention a view of magnamosis system 600. Both implants 610 and 620 do have through holes.

Accordingly, FIGS. 2-4 show magnamosis systems 200, 300 and 400, which are the same as system 100 shown in FIG. 1, with the difference of the addition of a force sensor 210, 310 and 410 respectively. Each of the force sensors, in the different examples of FIGS. 2-4, measures the attractive magnetic force caused by the two magnets during the magnetic mating of the two surfaces.

FIG. 2 shows force sensor 210 inside the first casing 112 located underneath the convex mating surface 116 (i.e. in between convex mating surface 116 and first magnet 114). FIG. 3 shows force sensor 310 inside the second casing 122 located underneath the concave mating surface 126 (i.e. in between concave mating surface 126 and second magnet 124).

Force sensors 210 and 310 could be various types of force sensors. In one example, the force sensor, resistor or gauge could ensure that the magnamosis system is exerting a force above a certain threshold or resistance. Such a sensor acts like an on/off sensor and be triggered when a certain force threshold is reached. An example of a force threshold for clinical use is approximately 4 N (1 lb) and the sensitivity does not have to be very high. In case the threshold is reached, the circuit closes and transmits a signal (e.g. wirelessly) via radio frequency identification technology. An external reader both wirelessly powers the internal device as well as reads the signal to ensure the implanting surgeon that the correct force has been met and the device will function as intended. The signal from the force sensor could also be translated to a visual or audible signal that alerts the surgeon that a threshold pressure has been achieved.

In another example of force sensors 210 and 310, one could have a calibrated spring. The spring is calibrated so that when the two implant surfaces are mating and the proper attractive force between the magnets is achieved the spring compresses completely. When the magnet is suspended in the center of the casing indicating no coupling a dark line painted on the magnet is visible through a small opening in an opaque material lining the casing. When for example the first implant couples with the second implant and compresses the spring the dark line is hidden and the reflective surface of the magnet is exposed through the opening. This then could serve as a visual indicator if the surgeon had visual contact with the magnamosis system. If the clinical procedure prevents direct visualization of the magnamosis system, it can be mounted on a delivery device that contains an integrated light (e.g. LED) and a photo detector. The light and photo detector would be oriented such that both were facing the magnamosis system and lined up with the small opening in the opaque material mentioned above. When the magnamosis system is not coupled with another device the dark line on the magnet is visible through the opening and the photo detector will detect very little light reflected from light source. However, when an implant is coupled, the reflective surface of the magnet will be visible through the opening and the photo detector will see a large amount of light reflected from the light source. This signal from the photo detector can be directly correlated to how much the spring has deflected and therefore how much attraction force there is between the magnets of the two implants.

In still another example, FIG. 4 shows a Hall effect sensor 410 to indirectly sense a magnetic field strength (flux) caused by the two magnets, 114 and 124. Hall effect sensor 410 can be embedded in, located outsides or near the magnamosis system 400 as long as it is able to detect the magnetic flux caused by the two magnets. For example, when the second implant 120 mates with the first implant 110, the magnetic flux will increase by an amount that is directly related to the attractive force between the two implants. The force between the implants is a function of distance and magnetic strength. By measuring the increase (or change) in magnetic flux, the amount of force can be determined by indirectly measuring the distance between the magnets. The measured or determined data can then be displayed to the surgeon.

Figure 7:
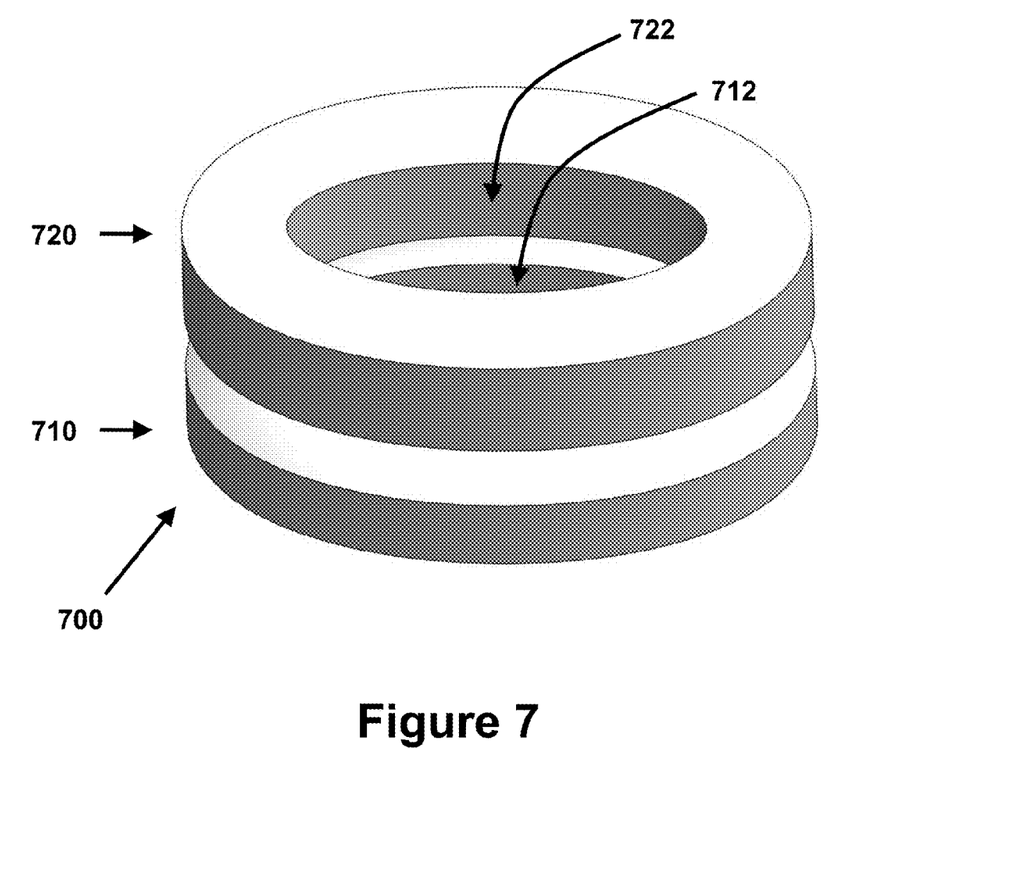
FIG. 7 shows according to an exemplary embodiment of the invention a view of magnamosis system 700. Both implants 710 and 720 have oval/ellipsoidal shaped through holes.

The implants of the magnamosis system according to the invention could be with or without through holes. The examples of FIGS. 1-5 are implants without through holes, whereas the examples of FIGS. 6-12 are with through holes. The magnamosis system 500 shows first implant 510 and second implant 520 analogous to two discs or two English muffins. The magnamosis system 600 shows first implant 610 and second implant 620 analogous to two Donuts with through holes 612 and 622, respectively. The implants could be circular or ellipsoidal/oval. FIG. 7 shows a magnamosis system 700 where implants 710 and 720 as well as the respective through holes 712 and 722 have an oval shape. Irrespective of the size or shape, the implants conform to the convex and concave mating surfaces with different radii as described supra.

The choice of the shape of the magnamosis system and existence of through holes depends on the clinical applicability and use. Different sizes and shapes of the device accommodate different clinical situations. As one might expect, a smaller person will most likely require a smaller bowel anastomosis than a larger person would. The simplest solution to accommodate these clinical issues is to have different diameter devices. However, this may not provide the best solution for every case. With a circular magnamosis system one can only create an anastomosis that is less than the diameter of that patient's bowel. In some clinical applications, it may be advantageous to create a larger anastomosis.

A larger anastomosis can be obtained by an anastomosis system with an oval shape according to FIG. 7. The oval shape increases the area of the anastomosis without increasing the space necessary to implant it. The oval does need not to be a traditional oval shape. The long edges of the oval could be parallel to further increase the size of the hole, but it is not necessary that they be so.

Figure 12:
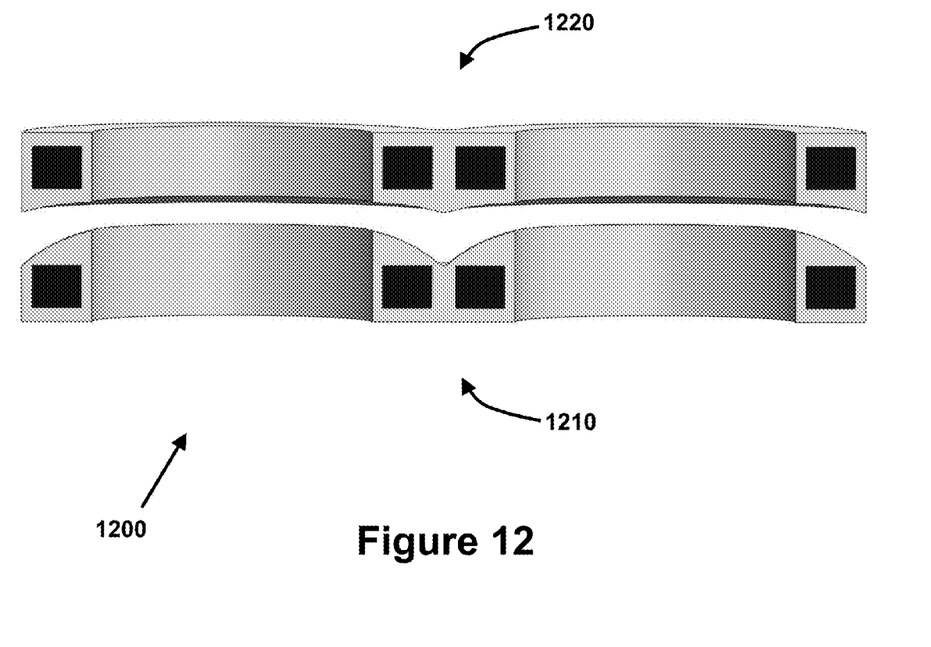
FIG. 12 shows according to an exemplary embodiment of the invention a system 1200 with a set of integrated first implants 1210 and a set of to integrated second implants 1220.

A larger or different type of anastomosis could also be achieved by having sets of multiples of the first and second implants forming a magnamosis system. FIG. 12 shows an example with two first implants 1210 and two second implants 1220. The implants in each set could be encased in the same casing, or somehow attached to each other. It is important to note that the convex and concave mating surfaces with different radii as described supra remains in place for each implant in the respective sets. One can image various structures, arrays and shapes varying based on the example of FIG. 12 all of which are part of the scope of the invention.

Figure 8:
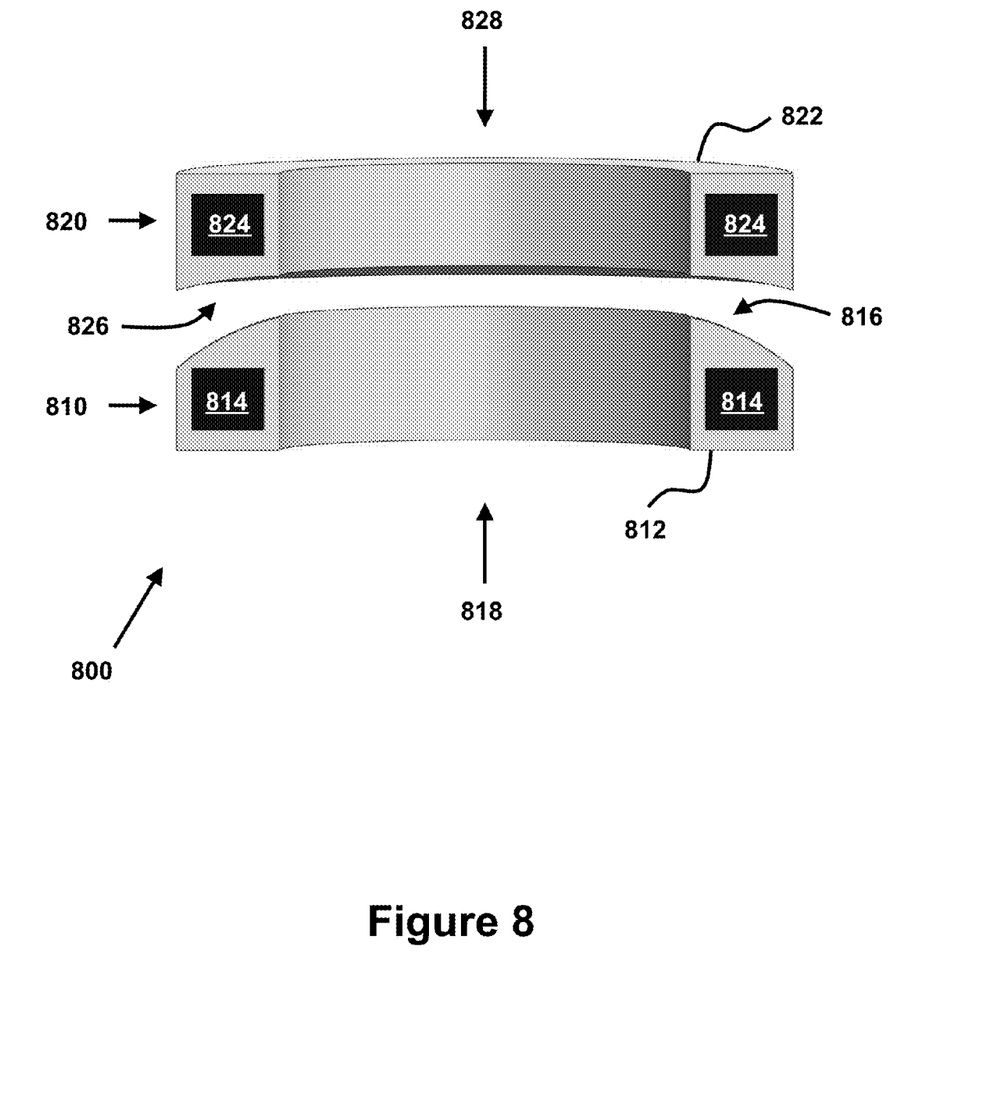
FIG. 8 shows a magnamosis system 800 with a first implant 810 and a second implant 820 for performing an anastomosis according to an exemplary embodiment of the invention. Both implants 810 and 820 have through holes.

FIG. 8 shows a magnamosis system 800 with a first implant 810 and a second implant 820. First implant 810 has a first casing 812 (defining a body) that encloses a first magnet 814 with a first magnetic polarity. First casing 812 further has a first through hole 818 and a terminal structure defining a convex mating surface 816 with a first radius.

Second implant 820 has a second casing 822 (defining a body) that encloses a second magnet 824 with a second magnetic polarity opposite from the first magnetic polarity. Second casing 822 further has a second through hole 828 and a terminal structure defining a concave mating surface 826 that extends within the body of the second implant 820. Concave mating surface 826 has a second radius, whereby the second radius is greater than the first radius as shown in FIG. 8. In one example, the convex mating surface is a single convex mating surface and the concave mating surface is a single concave mating surface.

While the convex mating surface 816 faces the concave mating, surface 826, a magnetic mating of the two surfaces, caused by the two magnets, causes the convex mating surface 816 of the first implant 810 to extend within the body of the second implant 820 and apply a non-uniform compressive force across two adjacent structures disposed in between the two mating surfaces. The non-uniform compressive force is capable of forming an anastomosis between the two adjacent structures. In addition, the non-uniform compressive force across the two adjacent structures increases radially inward toward the first and second through-holes, 818 and 828.

Figure 9:
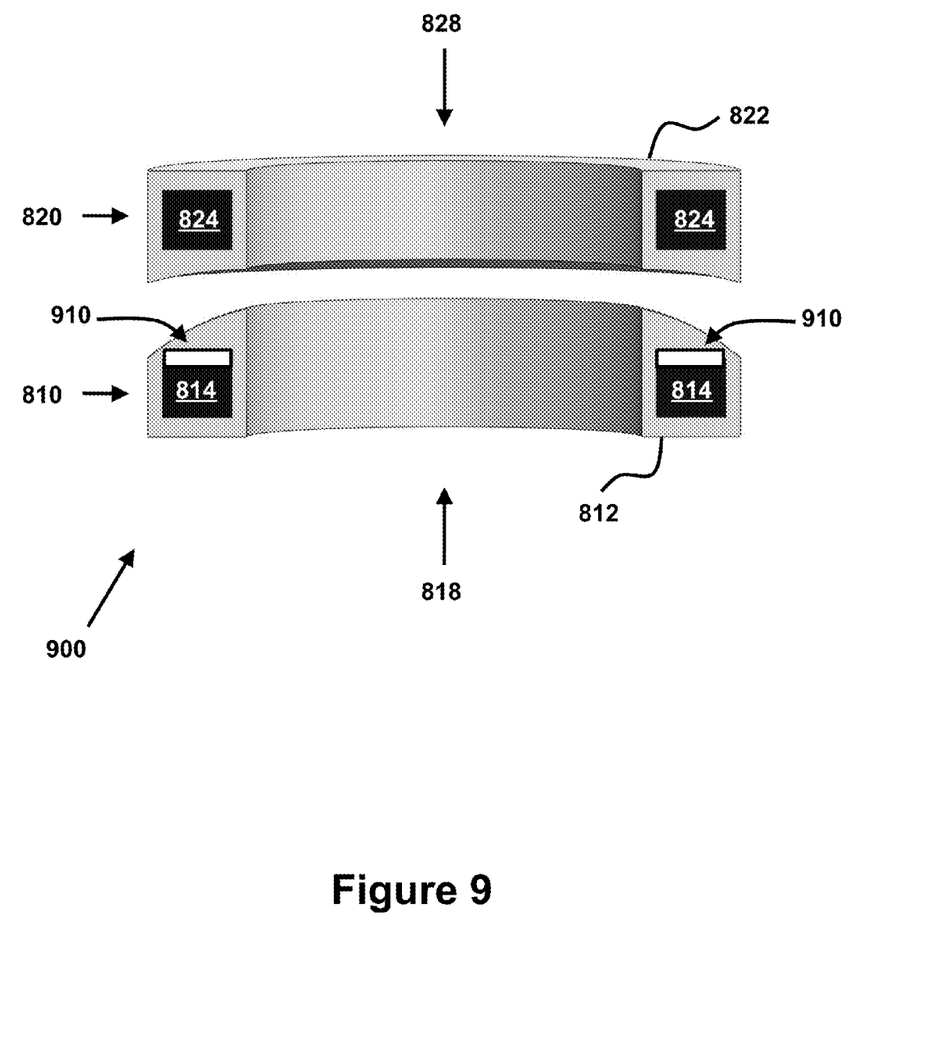
FIGS. 9-11 show magnamosis systems 900, 1000 and 1100 similar to magnamosis system 800 with the difference of also having force sensors 910, 1010 and 1110, respectively.
Figure 10:
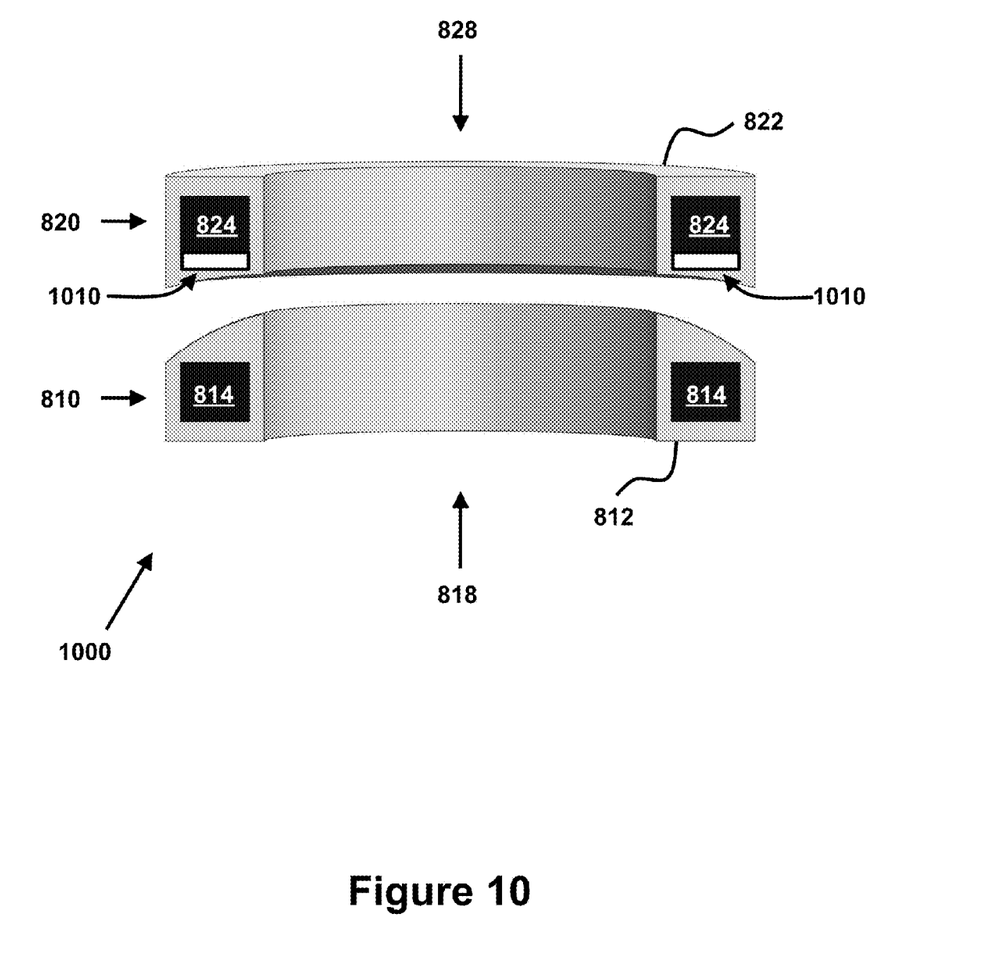
Figure 11:
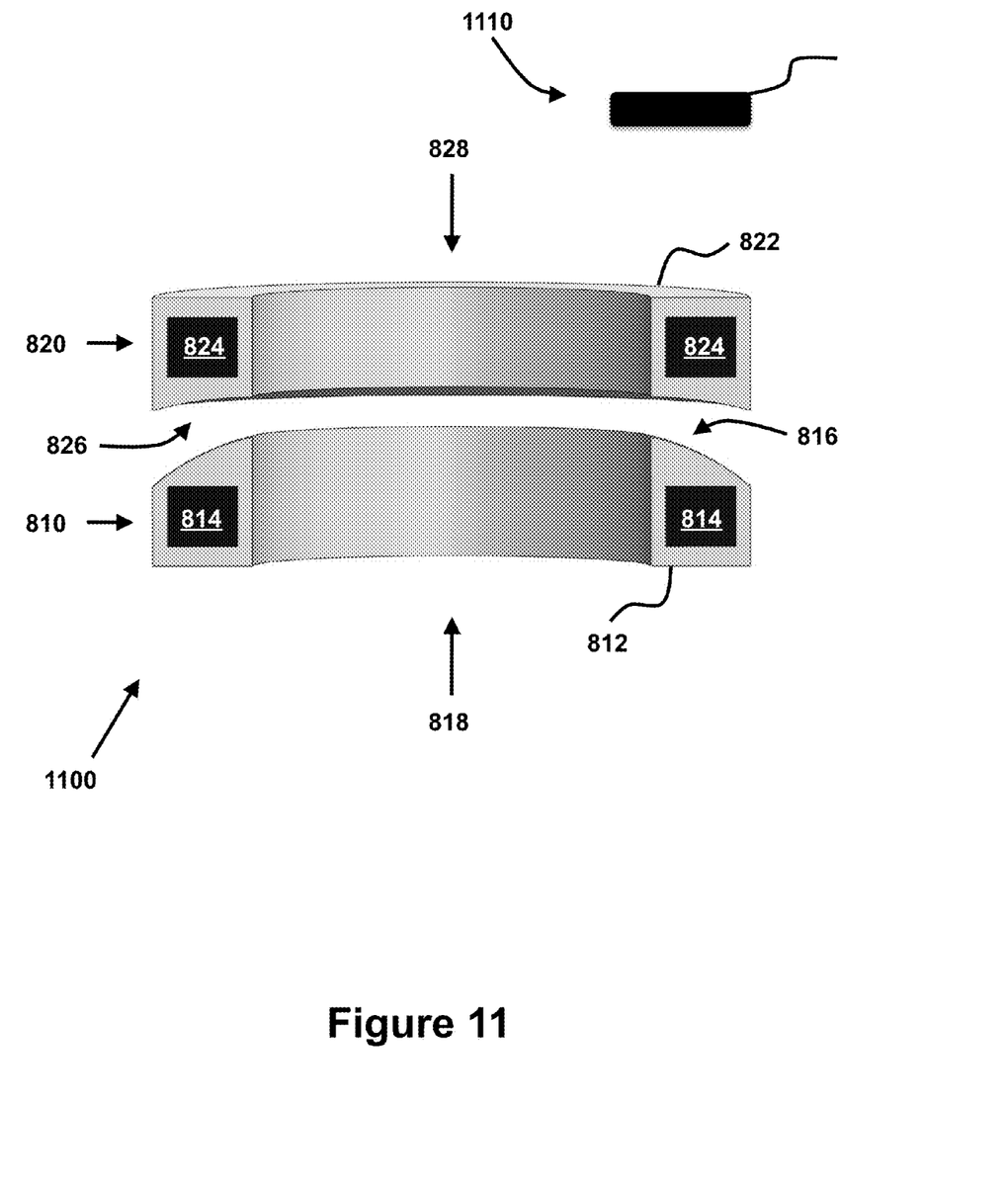

Accordingly, FIGS. 9-11 show magnamosis systems 900, 1000 and 1100, which are the same as system 800 shown in FIG. 8, with the difference of the addition of a force sensor 910, 1010 and 1110 respectively. Each of the force sensors, in the different examples of FIGS. 9-11, measures the attractive magnetic force caused by the two magnets during the magnetic mating of the to surfaces.

FIG. 9 shows force sensor 910 inside the first casing 812 located underneath the convex mating surface 816 (i.e. in between convex mating surface 816 and first magnet 814). FIG. 10 shows force sensor 1010 inside the second casing 822 located underneath the concave mating surface 826 (i.e. in between concave mating surface 826 and second magnet 824). In still another example, FIG. 11 shows a Hall effect sensor 1110 to indirectly sense a magnetic field strength (flux) caused by the two magnets, 814 and 824. The examples of sensors described with respect to FIG& 2-4 would apply to the example of sensor for FIG. 941.

In general and applicable to the embodiments described herein, the non-uniform compressive force could be strong enough to generate a necrosis tissue region of two adjacent structures. The necrosis tissue region could depart from the two adjacent structures to form a flow passage. Such a flow passage could form a fistula, and the fistula could pass the implants therethrough. Furthermore, the non-uniform compressive force could generate a force at the perimeter of the implants that is strong enough to fuse two adjacent structures while still promoting tissue growth within the two fused structures, The casing for each implant can either fully enclose the magnet and force sensor if applicable. However, this does not have to be the case since it is only important that the mating surface are fully covered or enclosed and that the magnet and/or force sensor remain one unit. For example, aspects of the non-facing sides could remain open, i.e. not enclosed. Therefore, we refer to the fact that the casings at least partially enclosed the magnets.

The casings could be made out of plastic like a polycarbonate, but any other material is applicable as long as it does not interfere with the magnetic fields of the magnets. The size and shape of the magnets could vary as long as they are capable of generating the non-uniform compressive force as described. The location of magnets inside the casing could vary, but it is typically important that they cover a large enough area to again generate the non-uniform compressive force. The magnets in general extend underneath the surface area of mating surfaces.

Force sensors could be combined. For example, one could have a magnamosis system with force sensors in each implant as well as a Hall effect sensor. One can imagine various combinations of sensors which are all applicable and useful to the invention.

Further teachings and embodiments are described in U.S. patent application Ser. No. 12/189,330 filed Aug. 11, 2008 now U.S. Pat. No. 8,142,454 issued on Mar. 27, 2012, which is herein incorporated by reference in its entirety.

The invention claimed is:

1. An anastomosis system, comprising:
   (a) a first implant, comprising: a body, a first casing, wherein said first casing at least partially encloses a first magnet with a first magnetic polarity, wherein said first casing defines a convex mating surface, and wherein said convex mating surface has a first radius; and
   (b) a second implant, comprising: a body, a second casing, wherein said second casing at least partially encloses a second magnet with a second magnetic polarity opposite from said first magnetic polarity, wherein said second casing defines a concave mating surface, wherein said concave mating surface extends within the body of said second implant, and wherein said concave mating surface has a second radius, wherein said second radius is greater than said first radius,
   wherein when said convex mating surface faces said concave mating surface, a magnetic mating of said surfaces, caused by said magnets, causes the convex mating surface of the first implant to extend within the body of the second implant and apply a non-uniform compressive force across two adjacent structures disposed in between said two mating surfaces, wherein said non-uniform compressive force is capable of forming an anastomosis between said two adjacent structures.

2. The system as set forth in claim 1, wherein said first casing further comprises a force sensor for measuring a force caused by said magnetic mating of said surfaces, wherein said force sensor is located underneath said convex mating surface.

3. The system as set forth in claim 1, wherein said second casing further comprises a force sensor for measuring a force caused by said magnetic mating of said surfaces, wherein said force sensor is located underneath said concave mating surface.

4. The system as set forth in claim 1, further comprising a Hall effect sensor to indirectly sense a magnetic field strength caused by said magnets.

5. The system as set forth in claim 1, wherein (i) said first casing fully encloses said first magnet, (ii) said second casing fully encloses said second magnet, or a combination thereof.

6. The system as set forth in claim 1, wherein (i) said first magnet is situated within said first casing and extends underneath the surface area of said convex mating surface, and (ii) said second magnet is situated within said second casing and extends underneath the surface area of said concave mating surface.

7. The system as set forth in claim 1, wherein (i) said first implant further comprises a first through hole and a terminal structure defining said convex mating surface, and (ii) said second implant further comprises a second through hole and a terminal structure defining said concave mating surface.

8. The system as set forth in claim 7, wherein said non-uniform compressive force across said two adjacent structures increases radially inward toward said first and second through-holes.

9. The system as set forth in claim 1, wherein the non-uniform compressive force across the two adjacent structures increases radially inward toward the center of the two surfaces.

10. The system as set forth in claim 1, wherein said non-uniform compressive force is strong enough to generate a necrosis tissue region of said two adjacent structures.

11. The system as set forth in claim 10, wherein said necrosis tissue region departs from said two adjacent structures to form a flow passage.

12. The system as set forth in claim 11, wherein said flow passage forms a fistula, wherein said fistula passes said implants therethrough.

13. The system as set forth in claim 1, wherein said non-uniform compressive force comprises a force at the perimeter of said implants that is strong enough to fuse said two adjacent structures while still promoting tissue growth within said two fused structures.

14. The system as set forth in claim 1, wherein said convex mating surface is a single convex mating surface.

15. The system as set forth in claim 1, wherein said concave mating surface is a single concave mating surface.

16. The system as set forth in claim 1, wherein said system comprises a set of multiples of said first implant forming a first integral implant and the same set of multiples of said second implant forming a second integral implant.

\* \* \* \* \*